(12) United States Patent
Cho et al.

(10) Patent No.: US 12,016,821 B2
(45) Date of Patent: Jun. 25, 2024

(54) NEEDLE ASSEMBLIES CONTAINING ORIENTED ACUPUNCTURE NEEDLES AND METHODS FOR PRODUCTION THEREOF

(71) Applicant: Abbott Diabetes Care Inc., Alameda, CA (US)

(72) Inventors: Hyun Cho, Berkeley, CA (US); Yi Wang, San Ramon, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 271 days.

(21) Appl. No.: 17/269,595

(22) PCT Filed: Aug. 22, 2019

(86) PCT No.: PCT/US2019/047668
§ 371 (c)(1),
(2) Date: Feb. 19, 2021

(87) PCT Pub. No.: WO2020/041571
PCT Pub. Date: Feb. 27, 2020

(65) Prior Publication Data
US 2021/0308009 A1    Oct. 7, 2021

Related U.S. Application Data

(60) Provisional application No. 62/721,711, filed on Aug. 23, 2018.

(51) Int. Cl.
*A61H 39/08* (2006.01)
*A61B 5/00* (2006.01)
(Continued)

(52) U.S. Cl.
CPC ......... *A61H 39/086* (2013.01); *A61B 5/6848* (2013.01); *B29C 45/14065* (2013.01);
(Continued)

(58) Field of Classification Search
CPC .... A61H 39/08; A61H 39/083; A61H 39/086; A61B 5/6848; B29C 45/14065; B65D 85/24
See application file for complete search history.

(56) References Cited

U.S. PATENT DOCUMENTS 3,768,635 A * 10/1973 Eggert .................. A61M 5/002
206/503
4,488,393 A * 12/1984 dinh Can ............... A61H 39/08
53/450

(Continued)

FOREIGN PATENT DOCUMENTS

| CN | 2277259 Y | 4/1998 |
|---|---|---|
| CN | 201058116 Y | 5/2008 |

(Continued)

OTHER PUBLICATIONS

ISRWO for related PCT/US2019/047668 with mail date of Apr. 3, 2020.

(Continued)

*Primary Examiner* — Todd J Scherbel
(74) *Attorney, Agent, or Firm* — ONE LLP

(57) ABSTRACT

Acupuncture needles may be used for piercing tissue with less trauma than may occur when employing larger gauge needles. However, because acupuncture needles are fabricated and packaged differently than are larger gauge needles, acupuncture needles may be less compatible with certain manufacturing processes. Needle assemblies compatible with manufacturing processes may comprise a continuous support material having a plurality of apertures defined therein, and a first injection molded coupler that surrounds a proximal portion of an acupuncture needle and connects the acupuncture needle to a first location upon the continuous support material, such that the acupuncture needle is held in a pre-determined orientation with respect to a (Continued)

longitudinal axis of the first injection molded coupler. The acupuncture needles in adjacent apertures may also be spaced apart substantially uniformly.

17 Claims, 11 Drawing Sheets

(51) Int. Cl.
*B29C 45/14* (2006.01)
*B29C 45/00* (2006.01)
*B29L 31/00* (2006.01)

(52) U.S. Cl.
CPC .... *B29C 45/14598* (2013.01); *A61H 2230/20* (2013.01); *B29C 2045/0089* (2013.01); *B29C 2045/14131* (2013.01); *B29C 2045/14327* (2013.01); *B29L 2031/759* (2013.01)

(56) References Cited

U.S. PATENT DOCUMENTS

| | | | |
|---|---|---|---|
| 6,231,584 B1* | 5/2001 | Gavronsky | A61H 39/08 606/189 |
| 8,226,540 B1* | 7/2012 | Chi | A61H 39/086 606/189 |
| 9,186,098 B2 | 11/2015 | Lee et al. | |
| 9,402,570 B2 | 8/2016 | Pace et al. | |
| 10,674,944 B2 | 6/2020 | Pace | |
| 2005/0021067 A1* | 1/2005 | Kim | A61H 39/08 606/189 |
| 2006/0173478 A1 | 8/2006 | Schraga | |
| 2011/0213225 A1 | 9/2011 | Bernstein et al. | |
| 2014/0171771 A1 | 6/2014 | Feldman et al. | |
| 2015/0352007 A1* | 12/2015 | Shayle | A61H 39/086 606/189 |
| 2016/0008028 A9 | 1/2016 | Matsumoto et al. | |
| 2016/0331283 A1 | 11/2016 | Rao et al. | |
| 2016/0331284 A1 | 11/2016 | Pace | |
| 2017/0196487 A1 | 7/2017 | Feldman et al. | |
| 2018/0235520 A1 | 8/2018 | Rao et al. | |
| 2019/0282137 A1 | 9/2019 | Stafford | |
| 2019/0347086 A1 | 11/2019 | Kiaie et al. | |
| 2020/0196919 A1 | 6/2020 | Rao et al. | |
| 2021/0219887 A1 | 7/2021 | Yee et al. | |
| 2022/0183595 A1 | 6/2022 | Wang et al. | |

FOREIGN PATENT DOCUMENTS

| | | |
|---|---|---|
| CN | 201295380 Y | 8/2009 |
| CN | 202096441 U | 1/2012 |
| CN | 104721042 A | 6/2015 |
| EP | 3 766 408 A1 | 1/2021 |
| JP | 8-173504 A | 7/1996 |
| JP | 2003-116962 A | 4/2003 |
| JP | 2013-066531 A | 4/2013 |
| JP | 2013-166363 A | 8/2013 |
| JP | 2018-021811 A | 2/2018 |
| WO | WO 01/58348 A2 | 8/2001 |
| WO | WO 2013/100057 A1 | 7/2013 |
| WO | WO 2013/144255 A1 | 10/2013 |
| WO | WO 2014/111681 A2 | 7/2014 |
| WO | WO 2018/136898 A1 | 7/2018 |
| WO | WO 2019/236850 A1 | 12/2019 |
| WO | WO 2019/236859 A1 | 12/2019 |
| WO | WO 2019/236876 A1 | 12/2019 |
| WO | WO 2020/041571 A1 | 2/2020 |

OTHER PUBLICATIONS

CA, 3,107,79 Examiner's Report, Jan. 11, 2022.
EP, 19763147.6 Examination Report, Dec. 21, 2023.
CN, 201980055443.1 First Office Action, Jan. 30, 2024.
JP, 2023-094274 Office Action, Mar. 26, 2024.

* cited by examiner

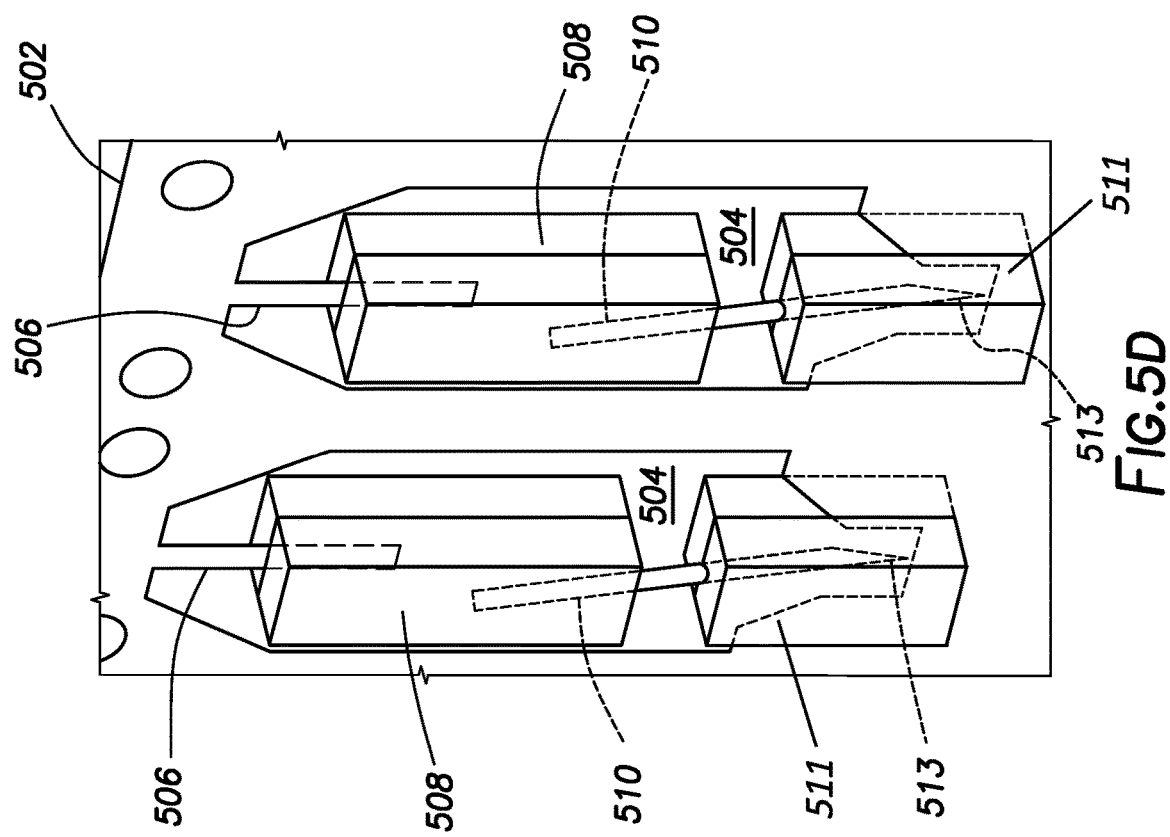
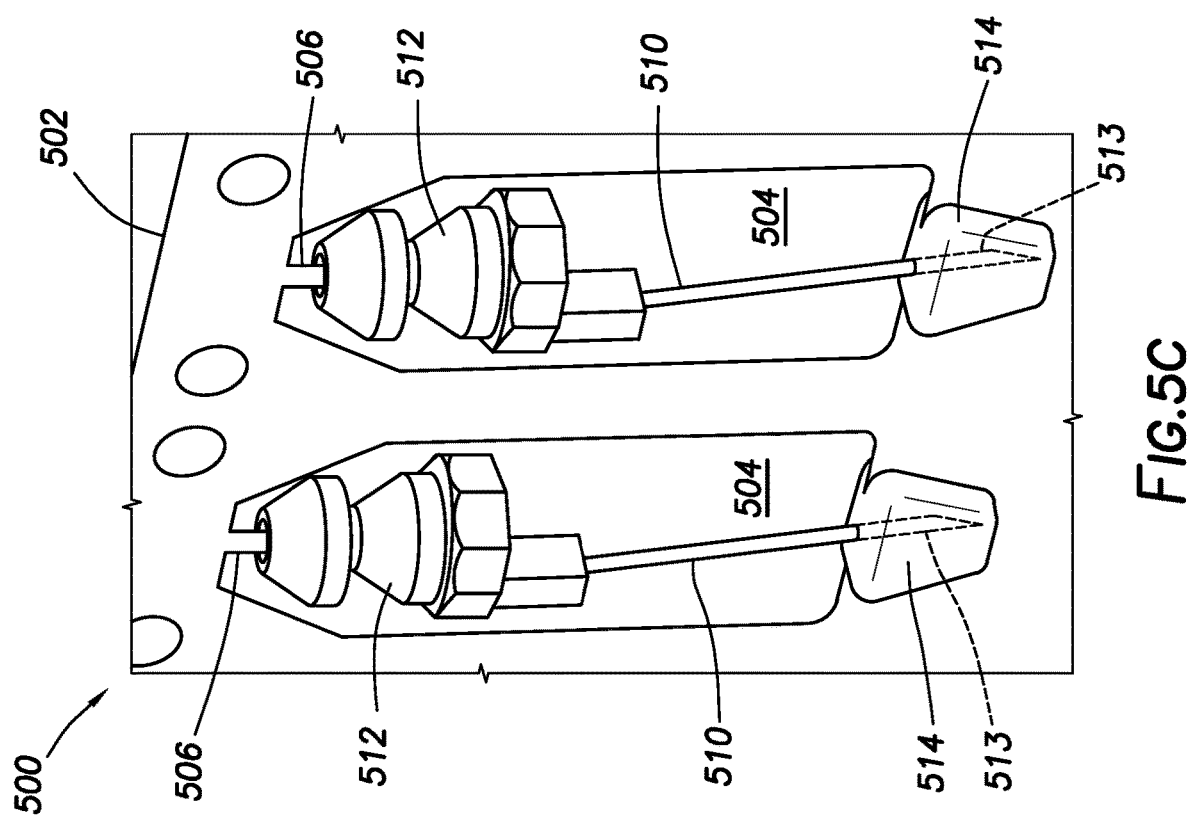

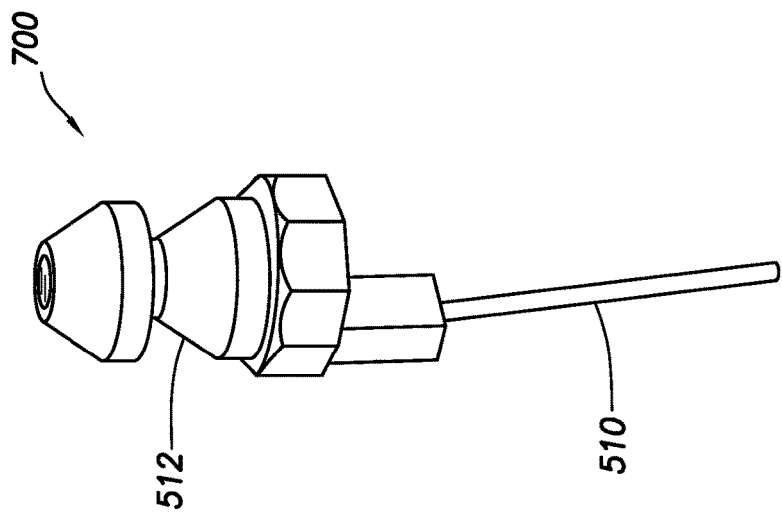
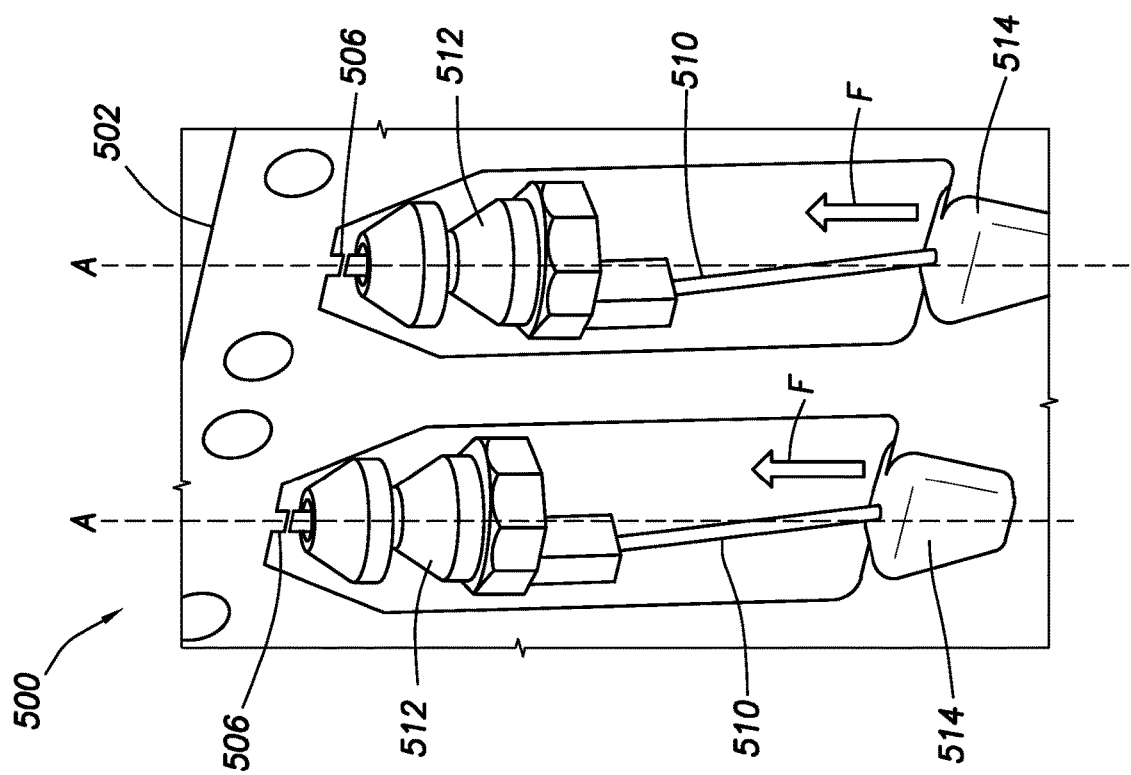
FIG.8B
FIG.8A

NEEDLE ASSEMBLIES CONTAINING ORIENTED ACUPUNCTURE NEEDLES AND METHODS FOR PRODUCTION THEREOF

BACKGROUND

The detection of various analytes within an individual can sometimes be vital for monitoring the condition of their health. Deviation from normal analyte levels can often be indicative of a number of physiological conditions. Glucose levels, for example, can be particularly important to detect and monitor in diabetic individuals. By monitoring glucose levels with sufficient regularity, a diabetic individual may be able to take corrective action (e.g., by injecting insulin to lower glucose levels or by eating to raise glucose levels) before significant physiological harm occurs. Other analytes commonly subject to physiological dysregulation that may similarly be desirable to monitor include, but are not limited to, lactate, oxygen, pH, A1c, ketones, drug levels, and the like.

Analyte monitoring in an individual may take place periodically or continuously over a period of time. Periodic analyte monitoring may take place by withdrawing a sample of bodily fluid, such as blood, at various time intervals and analyzing ex vivo. Continuous analyte monitoring may be conducted using one or more sensors that remain at least partially implanted within a tissue of an individual, such as dermally, subcutaneously, or intravenously, so that analyses may be conducted in vivo. Implanted sensors may collect analyte data continuously or sporadically (usually at regular intervals), depending on an individual's particular health needs and/or previously measured analyte levels.

Periodic ex vivo analyte monitoring can be sufficient to determine the physiological condition of many individuals. However, ex vivo analyte monitoring may be inconvenient or painful for some individuals. Moreover, there is no way to recover lost data if a measurement is not obtained at an appropriate time.

Continuous analyte monitoring with an in vivo implanted sensor may be a more desirable approach for individuals having severe analyte dysregulation and/or rapidly fluctuating analyte levels, although it can also be beneficial for other individuals as well. While continuous analyte monitoring with an implanted sensor can be advantageous, there are challenges associated with these types of measurements. Intravenous analyte sensors have the advantage of providing analyte concentrations directly from blood, but they are invasive and can sometimes be painful for an individual to wear over an extended period. Subcutaneous and dermal analyte sensors can often be less painful for an individual to wear and can provide sufficient measurement accuracy in many cases.

The active portion of an analyte sensor may enter an individual's body through a skin penetration (e.g., transcutaneously) or other tissue penetration, with one or more additional sensor components remaining external to the individual's body. An introducer, particularly a needle or similar sharp, may be used to facilitate insertion of a subcutaneous or dermal analyte sensor into an individual's skin. The needle or similar sharp may make an initial penetration into the dermal layer of the skin, through which the analyte sensor may be subsequently inserted. For manufacturing reasons, discussed hereinafter, relatively large gauge needles or sharps may be used to facilitate insertion of an analyte sensor into a tissue. Needles having smaller diameters, such as acupuncture needles, may also be satisfactorily used, however. Smaller diameter needles may be particularly desirable for reducing tissue trauma at the site of sensor insertion, thereby increasing comfort for a wearer. Decreased tissue trauma may also limit the occurrence of erroneous or altered sensor readings in some instances.

Despite their desirability for promoting user comfort and potentially improving sensor performance, there is a significant manufacturing shortcoming associated with the use of acupuncture needles at present. Larger gauge needles or similar sharps may be manufactured with the needles or sharps held in highly oriented arrays and fixed in a defined configuration with respect to each other. The defined configuration of larger gauge needles may facilitate their incorporation into high-throughput manufacturing processes, particularly automated processes employing reel-to-reel production techniques. Acupuncture needles, in contrast, are commercially packaged in bulk in a randomized orientation. Although acupuncture needles may be incorporated into an inserter for an analyte sensor by manual 'pick and place' techniques, such approaches may considerably slow manufacturing throughput since they take place at the stage of assembling the finished sensor device. Accordingly, incorporating acupuncture needles in analyte sensor inserters currently presents economic and manufacturing challenges that may supersede the otherwise desirable benefits of employing acupuncture needles for insertion of an analyte sensor.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 5A-5C show diagrams illustrating an exemplary process whereby a first configuration of needle assemblies of the present disclosure may be fabricated. FIG. 5D shows a diagram illustrating an alternative injection molding process to that shown in FIG. 5B.

FIG. 8A shows an illustrative process to remove a needle construct from a needle assembly. FIG. 8B shows an illustrative needle construct freed from a support material.

DETAILED DESCRIPTION

Figure 1:
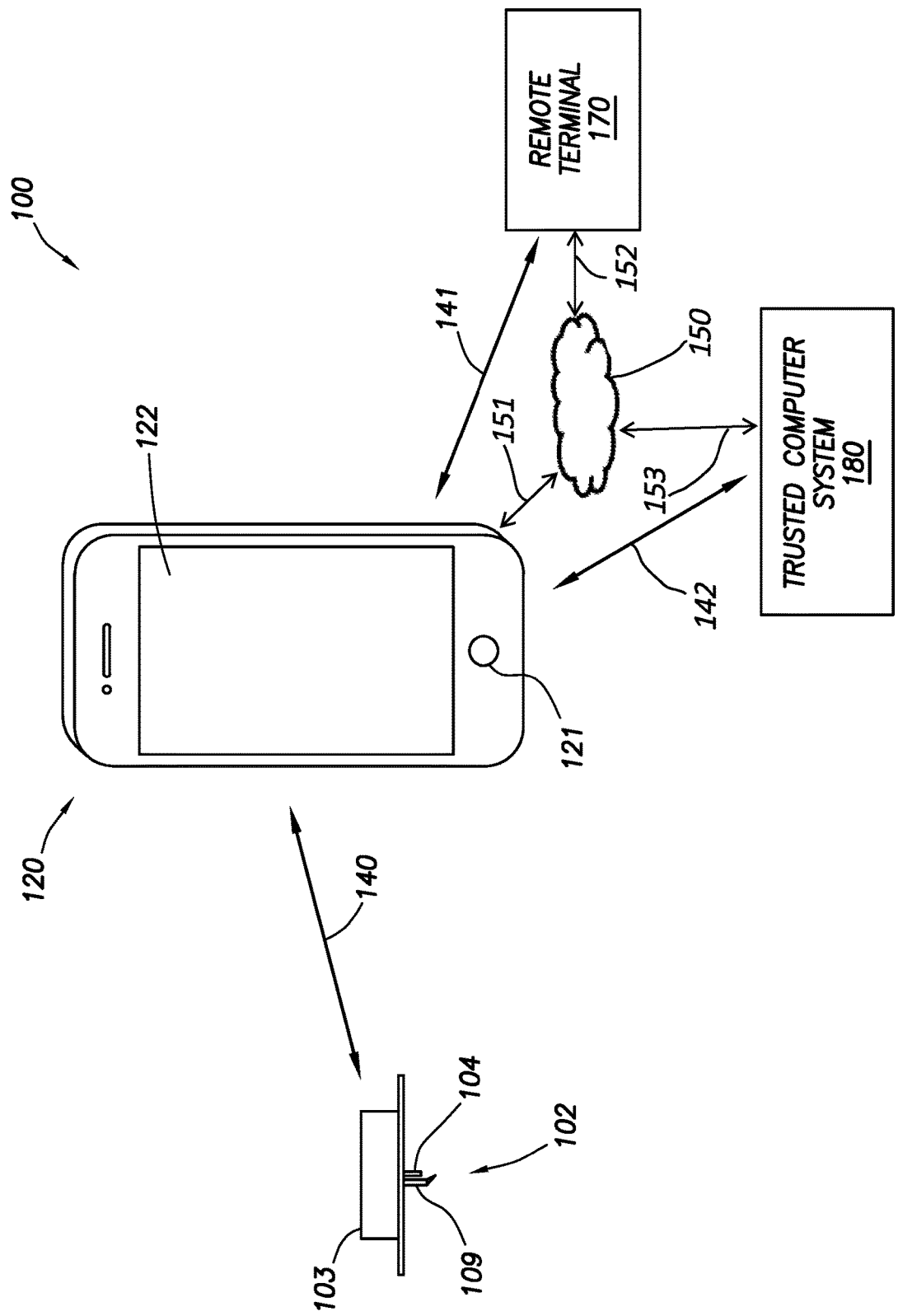
FIG. 1 shows a diagram of an illustrative analyte monitoring system that may incorporate an analyte sensor compatible with the disclosure herein.

The present disclosure generally describes analyte sensors suitable for in vivo use and, more specifically, oriented acupuncture needles and manufacturing methods associated therewith for use in conjunction with analyte sensors. Analyte sensor inserters incorporating an oriented acupuncture needle are also described herein.

As discussed above, utilization of an acupuncture needle for piercing tissue to facilitate insertion of an analyte sensor may be desirable. Use of an acupuncture needle may promote user comfort and decrease tissue trauma at the site of sensor insertion. Decreased tissue trauma may also advantageously improve sensor performance in certain cases. However, the randomized bulk packaging of acupuncture needles can complicate their utilization in certain high-throughput manufacturing processes. In particular, it can be difficult to orient as-obtained acupuncture needles in established high-throughput manufacturing processes for manufacturing an analyte sensor or analyte sensor inserter. As a result, substitution of acupuncture needles for larger gauge needles or similar sharps in certain high-throughput manufacturing processes may not be a straightforward matter. Nevertheless, the present disclosure demonstrates that pre-orientation of acupuncture needles in the manner disclosed herein may provide sufficient process compatibility to conduct high-throughput manufacturing. Namely, the present disclosure demonstrates that acupuncture needles may be pre-oriented in a batchwise manner prior to final assembly of a sensor device, and the oriented acupuncture needles may be satisfactorily incorporated in existing or modified of high-throughput manufacturing process for sensor assembly.

In various aspects, the present disclosure provides needle assemblies containing a plurality of acupuncture needles positioned in a pre-determined and highly oriented arrangement. Advantageously, acupuncture needles may be oriented with sufficient rapidity to support fabrication of the needle assemblies in a high-throughput manner. Alternately, stockpiling of the oriented acupuncture needles may occur for feeding to a high-throughput manufacturing process. Moreover, individual needle constructs may be readily removed from the needle assemblies with the needle orientation being maintained, again in a high-throughput manner, such that acupuncture needles may be incorporated in analyte sensor inserters in a similar manner to that used for larger gauge needles and sharps and using minimally modified manufacturing lines. As such, the needle assemblies disclosed herein may facilitate high-throughput manufacturing of analyte sensor inserters incorporating an oriented acupuncture needle. Depending on various manufacturing considerations, the needle assemblies described herein may be fabricated in a separate production line from the analyte sensor inserters (potentially with stockpiling of the needle assemblies), or fabrication of the needle assemblies may be directly coupled as a separate operation of a process line for fabricating an analyte sensor inserter.

In some embodiments, the needle assemblies described herein may contain a plurality of acupuncture needles connected to a continuous support material via at least a first injection molded coupler. As used herein, the term "continuous support material" refers to a material whose length is much longer than its width, such as a material available in rolled form and having an aspect ratio of at least about 10, at least about 100, at least about 1,000, or at least about 10,000. Manufacturing processes employing a continuous support material may convey the continuous support material from a first reel to a second reel, with acupuncture needles becoming connected (coupled) to the continuous support material in between the first and second reels. A continuous support material may facilitate fabrication of the needle assemblies disclosed herein via high-throughput manufacturing methods. It is to be appreciated, however, that the needle assemblies and processes of the present disclosure may be alternately formed or conducted with support materials having finite dimensions, such that the needle assemblies are manufactured in shorter lengths (discrete units) as well.

More specifically, the needle assemblies and processes described herein feature acupuncture needles that are individually oriented within a plurality of apertures defined in a support material prior to an injection molding operation that connects the acupuncture needles to the support material. In some embodiments, orientation of the acupuncture needles within the needle assemblies may take place offline (prior to a manufacturing process incorporating an acupuncture needle in a sensor inserter) to provide a stockpile of oriented acupuncture needles. For example, robotic or manual 'pick and place' techniques may be used to provide an initial orientation of the acupuncture needles prior to forming the needle assemblies as described herein. Once the acupuncture needles have been connected to the support material with consistent orientation and spacing, further processing of the needle assemblies in a subsequent or contiguous production line may be readily conducted. As such, the present disclosure may facilitate high-throughput production of analyte sensors that are capable of insertion into a tissue of interest with minimal trauma, thereby allowing various user benefits to be realized.

Before describing the present needle assemblies and associated methods of production and use in further detail, a brief overview of suitable in vivo analyte sensors and analyte sensor applicators will be provided for further context of the disclosure herein. It is to be appreciated, however, that analyte sensors and analyte sensor applicator having different architectures and components other than those expressly described may be suitably used as well.

FIG. 1 shows a diagram of an illustrative analyte monitoring system that may incorporate an analyte sensor compatible with the disclosure herein. As shown, analyte monitoring system 100 includes sensor control device 102 and reader device 120 that are configured to communicate with one another over a local or remote communication path or link, which may be wired or wireless, uni- or bi-directional, and encrypted or non-encrypted. Reader device 120 may be a multi-purpose smartphone or a dedicated electronic reader instrument. While only one reader device 120 is shown, more than one reader device 120 may be present in certain instances. Multiple reader devices 120 may be in communication with one another (e.g., to share and synchronize data). Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also be in communication with network 150 (e.g., a mobile telephone network, the Internet, or a cloud server) via communication path/link 151. Network 150 may be further communicatively coupled to remote terminal 170 via communication path/link 152 and/or trusted computer system 180 via communication path/link 153. Remote terminal 170 and/or trusted computer system 180, in turn, may communicate with network 150, in some embodiments. Alternately, sensor control device 102 may communicate directly with remote terminal 170 and/or trusted computer system 180 without an intervening reader device 120 being present. For example, sensor control device 102 may communicate with remote terminal 170 and/or trusted computer system 180 through a direct communication link to network 150, according to some embodiments, as described in U.S. Patent Application Publication 2011/0213225 and incorporated herein by reference in its entirety. Any suitable electronic communication protocol may be used for each of the local communication paths or links such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user. Reader device 120 may comprise display 122 and optional input component 121. Display 122 may comprise a touch-screen interface, according to some embodiments.

Sensor control device 102 includes sensor housing 103, which may include circuitry and a power source for operating sensor 104. Optionally, the power source and/or active circuitry may be omitted. Sensor 104 may comprise a sensor tail (active portion) having sufficient length for insertion at a desired depth into a tissue of interest, such as the dermal layer of the skin. The sensor tail may comprise a sensing region that is active for sensing, and may comprise an enzyme and/or a redox mediator, according to one or more embodiments. A polymeric membrane (mass transport limiting layer) may be disposed upon the sensor tail, or the whole sensor, to aid in regulating flux of an analyte of interest, according to some embodiments.

One or more analyte levels may be determined using sensor 104 and undergo communication to reader device 120. The analyte may be monitored in any biological fluid such as dermal fluid, plasma, blood, lymph, or the like. Analytes that may be monitored are not considered to be particularly limited. In certain embodiments, the analyte may be glucose. Other analytes of interest with respect to human physiology may include, for example, lactate, oxygen, pH, A1c, ketones, drug levels, and the like. Both single analytes and combinations of analytes may be assayed.

Sensor 104 extends adjacent to needle 109 in the configuration shown in FIG. 1. Needle 109 is present transiently just prior to insertion of sensor 104 into a tissue and is withdrawn thereafter. While present, needle 109 may facilitate insertion of sensor 104 into a tissue of interest by opening an access pathway for sensor 104 to follow. For example, needle 109 may facilitate penetration of the epidermis as an access pathway to the dermis to allow implantation of sensor 104 to take place, according to one or more embodiments. In illustrative embodiments, needle 109 may be solid or hollow, beveled or non-beveled, and/or circular or non-circular in cross-section. Once the sensor 104 has been inserted into a tissue, the needle 109 is withdrawn, removed, and no longer deployed or associated with sensor housing 103. That is, the needle is pulled back or otherwise retracted into the analyte sensor inserter 200.

In the configuration depicted in FIG. 1, a tip of needle 109 is angled over the terminus of sensor 104, such that needle 109 penetrates a tissue first and opens an access pathway for sensor 104. In alternative embodiments, the body of needle 109 may be angled with respect to sensor 104, such that needle 109 again penetrates a tissue of interest in advance of sensor 104. Angled configurations for needle 109 are described in further detail in commonly owned U.S. Patent Application Publication 2017/0196487, which is incorporated herein by reference in its entirety. In still other alternative embodiments, sensor 104 may reside within a lumen or groove of needle 109, with needle 109 similarly opening an access pathway for sensor 104 to follow. Regardless of configuration, once sensor 104 has been inserted into a tissue of interest, needle 109 may be retracted from the tissue and into an analyte sensor inserter (not shown in FIG. 1) so to that the risk of sharps exposure is minimized.

Sensors 104 compatible with analyte monitoring system 100 may comprise two-electrode or three-electrode detection motifs, according to various embodiments. Three-electrode detection motifs may comprise a working electrode, a counter electrode, and a reference electrode. Two-electrode detection motifs may comprise a working electrode and a second electrode, in which the second electrode functions as both a counter electrode and a reference electrode (i.e., a counter/reference electrode). In both two-electrode and three-electrode detection motifs, the active portion of analyte sensor 104 may be in contact with the working electrode. The various electrodes may be at least partially stacked upon one another or laterally spaced apart, with a dielectric separator being positioned in between. A mass transport or biocompatibilizing membrane may overcoat at least some of the electrodes, or the whole sensor, according to some embodiments of the present disclosure.

It is to be recognized that analyte monitoring system 100 may comprise additional features and functionality that are not necessarily described herein in the interest of brevity. Accordingly, the foregoing description of analyte monitoring system 100 should be considered illustrative and non-limiting in nature.

Figure 2:
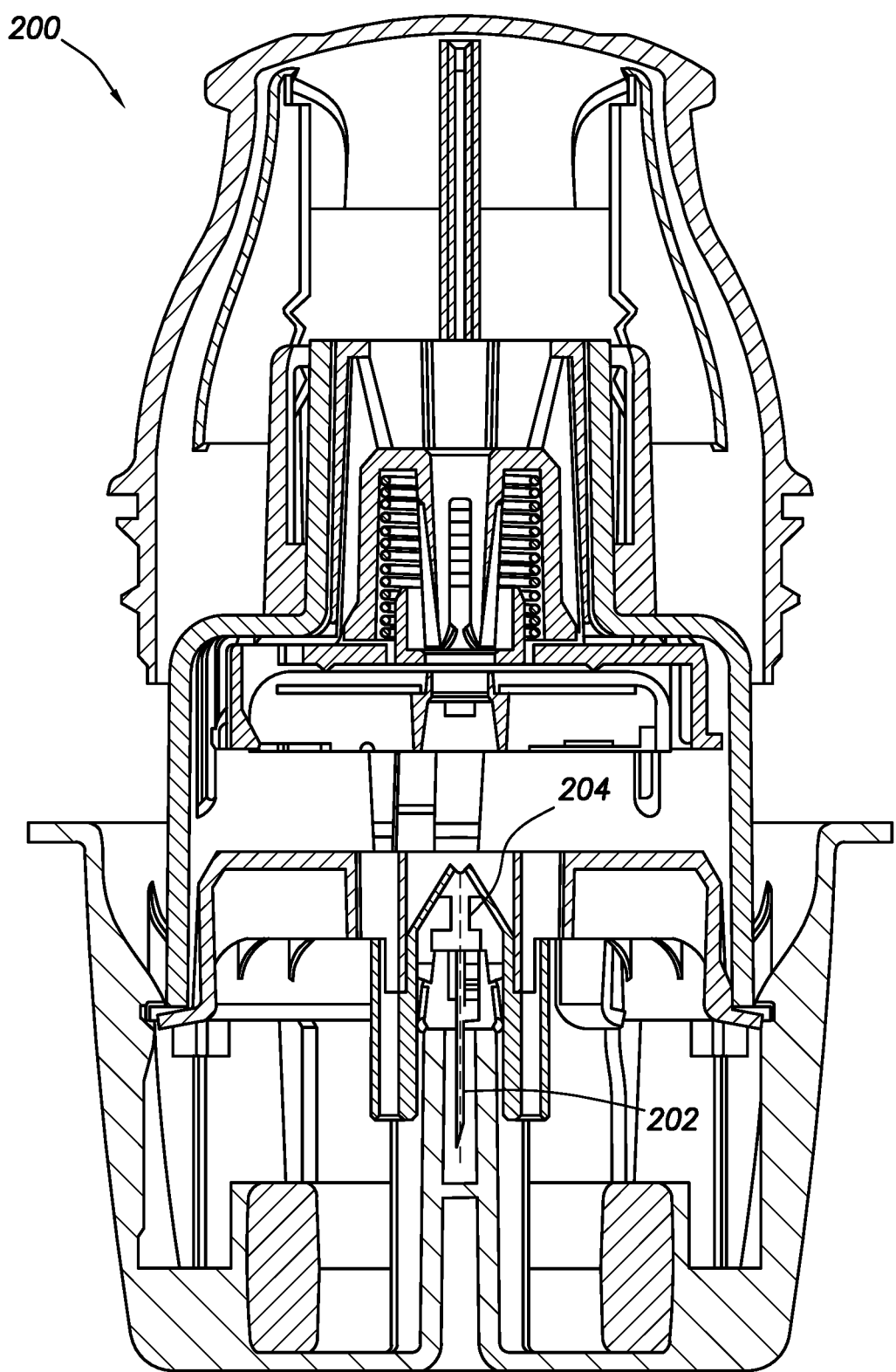
FIG. 2 shows a diagram of a portion of an illustrative analyte sensor inserter compatible with the disclosure herein.

Sensor 104 may be inserted in a tissue of interest using an analyte sensor inserter that is further operable to position sensor housing 103 upon the tissue surface, such as upon a surface of the skin. Illustrative analyte sensor inserters operable for positioning a sensor housing upon a skin surface are described in further detail in commonly owned U.S. Pat. Nos. 9,186,098 and 9,402,570 and commonly owned U.S. Patent Application Publication 2016/0331284, all of which are incorporated herein by reference in their entirety. FIG. 2 shows a diagram of a portion of illustrative analyte sensor inserter 200, in which needle 202 extends normally from needle holder 204 and promotes insertion of a dermal sensor, as described in greater detail in U.S. Pat. No. 9,402,570. As shown hereinafter, needle constructs similar in structure to needle holder 204 may be produced according to the disclosure herein.

Accordingly, needle assemblies and needle constructs of the present disclosure are described in further detail hereinafter and with further reference to the drawings. The needle assemblies and needle constructs described herein may be incorporated in an insertion device for an analyte sensor, also referred to herein as an analyte sensor inserter, according to various embodiments.

In various embodiments, needle assemblies of the present disclosure may comprise: a support material having a plurality of apertures defined therein, and a first injection molded coupler located within each aperture that surrounds a proximal portion of an acupuncture needle and connects the acupuncture needle to a first location upon the support material. The acupuncture needle is held in a pre-determined orientation with respect to a longitudinal axis of the first injection molded coupler. As used herein, the term "distal portion" refers to a location upon the shaft of an acupuncture needle that is nearer to the sharpened tip (i.e., the insertion tip), and the term "proximal portion" refers to a location upon the shaft of an acupuncture needle that is nearer to the end opposite the insertion tip. As used herein, the term "distal portion" includes a segment of the acupuncture needle that includes at least the insertion tip, and the term "proximal portion" includes a segment of the acupuncture needle that includes the end opposite the insertion tip.

Acupuncture needles suitable for use in the present disclosure are not considered to be particularly limited in size or length, unless otherwise indicated herein. In more specific embodiments, acupuncture needles suitable for use in the disclosure herein may range between about 0.1 mm and about 0.6 mm in diameter, or between about 0.15 and about 0.4 mm in diameter, or between about 0.25 mm and about 0.35 mm in diameter, including any value or sub-range therebetween.

According to more specific embodiments, each acupuncture needle within the needle assemblies may be held in substantially the same orientation, within manufacturing tolerances. In some or other more specific embodiments, the acupuncture needles in adjacent apertures may be spaced apart from one another substantially uniformly, within manufacturing tolerances. Angular deviation (variance) between the plurality of acupuncture needles in the needle assemblies may be about 1 degree or less, or about 0.5 degrees of less, or about 0.25 degrees or less. According to various embodiments, the pitch (spacing between adjacent acupuncture needles) may be about 15 mm or less, or about 12 mm or less, or about 10 mm or less, or about 7 mm or less, or about 5 mm or less, with a pitch variance of about 0.02 mm or less. In more specific embodiments, the pitch may constitute a spacing between about 8 mm and about 10 mm, with a pitch variance of about 0.02 mm or less. In some or other embodiments, the length of the acupuncture needles may be about 20 mm or less, or about 15 mm or less, or about 12 mm or less, or about 10 mm or less, or about 8 mm or less, with a length variance of about 0.05 mm or less. In more specific embodiments, the length of the acupuncture needles may range between about 9 mm and about 12 mm, or between about 10 mm and about 11 mm, with a length variance of about 0.05 mm or less.

According to some embodiments, the acupuncture needle within each aperture may be held non-parallel with respect to the longitudinal axis of the first injection molded coupler. In more specific embodiments, the acupuncture needle within each aperture may be held at an angle ranging between about 5° and about 15°, or between about 7° and about 12° or between about 8° and about 11° with respect to the longitudinal axis, including any value or sub-range therebetween. By angling the acupuncture needle, the skin may stretch to one side when making a skin penetration, which creates a gap for promoting easier sensor insertion. In still more specific embodiments, the acupuncture needle within each aperture may be held at an angle ranging between about 9° and about 10° with respect to the longitudinal axis, including any value or sub-range therebetween.

In certain embodiments, the needle assemblies described herein may further comprise a second injection molded coupler located within each aperture that surrounds a distal portion of the acupuncture needle and connects the acupuncture needle to a second location upon the support material. The second injection molded coupler may aid in protecting the insertion tip of the acupuncture needle during fabrication of the needle assemblies described herein, thereby potentially lowering the fraction of units rejected for quality control defects during subsequent analyte sensor inserter fabrication. Moreover, the second injection molded coupler may further stabilize the acupuncture needle within each aperture by limiting flexural motion during fabrication of the needle assemblies. Alternately, a second injection molded piece may surround a distal portion of the acupuncture needle but remain unattached (no coupling) to the support material. Such configurations may similarly aid in protecting the insertion tip of the acupuncture needle.

Figure 3:
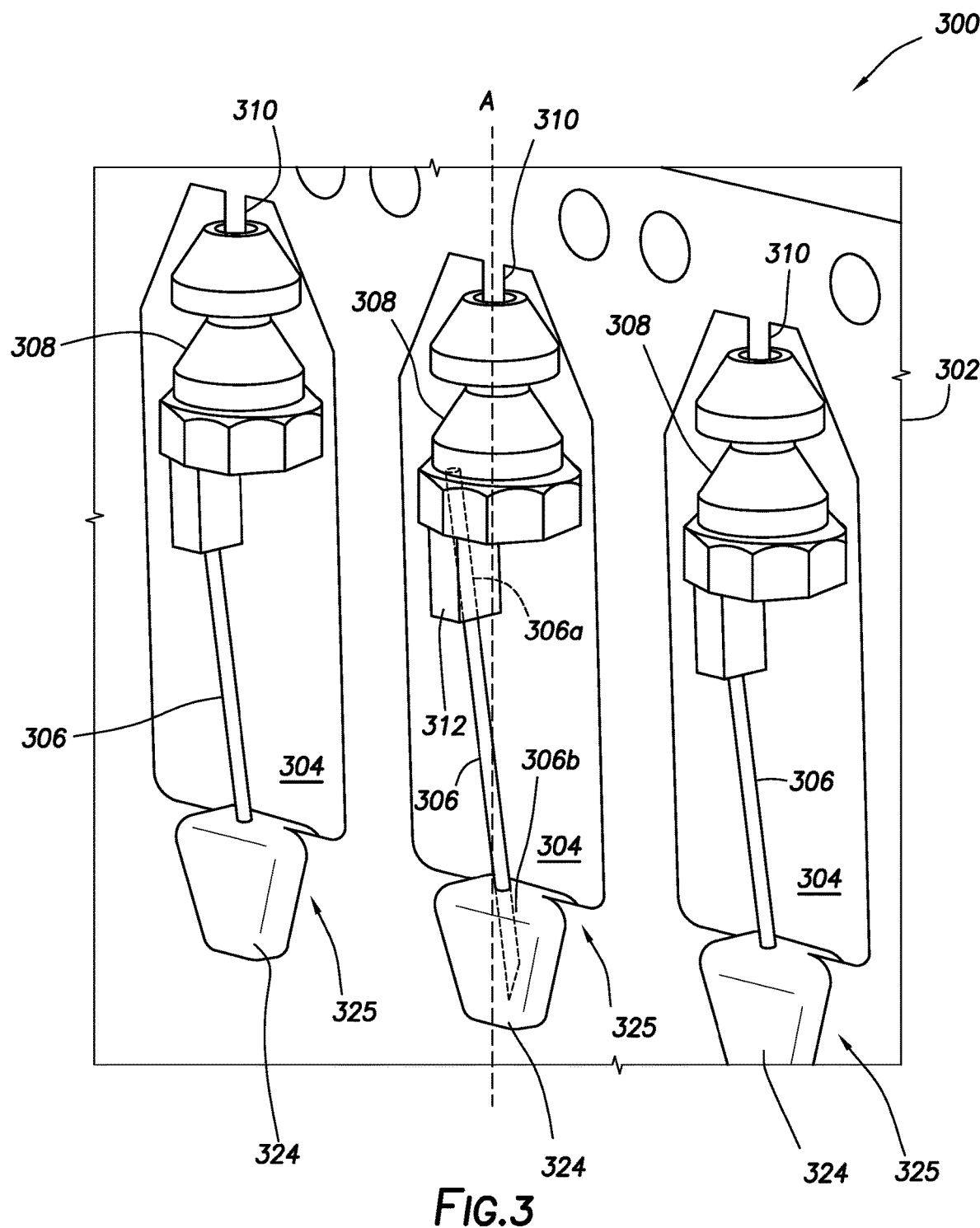
FIG. 3 shows a diagram of a portion of a needle assembly of the present disclosure having a plurality of acupuncture needles affixed in a pre-determined orientation.

FIG. 3 shows a diagram of a portion of a needle assembly of the present disclosure having a plurality of acupuncture needles affixed in a pre-determined orientation. As shown in FIG. 3, needle assembly 300 is formed upon continuous support material 302. Continuous support material 302 may be a continuous metal tape, strip or film, although alternative materials and forms capable of being processed in a reel-to-reel manner may also be used in some cases. In some embodiments, stainless steel may be a suitable metal upon which needle assembly 300 may be fabricated. Other suitable tapes may include alternative metals or other materials that are able to withstand the injection molding temperatures needed to fabricate needle assembly 300. In alternative embodiments, needle assembly 300 may be formed upon a support material having finite length, such that assembly fabrication takes place in discrete units rather than by reel-to-reel continuous processing.

Apertures 304 are defined in the plane of continuous support material 302, such as through a die-cutting or stamping process, for example. Formation of apertures 304 may take place in conjunction with or prior to the process for fabricating needle assembly 300, or apertures 304 may be present in as-obtained continuous support material 302.

Acupuncture needles 306 are affixed to continuous support material 302 in at least one location and may be arranged in-plane in each aperture 304. At least proximal portion 306a of each acupuncture needle 306 is surrounded by first injection molded coupler 308, which adjoins proximal portion 306a to continuous support material 302 via neck 310. Each neck 310 may extend from continuous support material 302 into each aperture 304, such that first injection molded coupler 308 surrounds neck 310. According to more specific embodiments, neck 310 may be coincident with longitudinal axis A of first injection molded coupler 308. As depicted in FIG. 3, neck 310 terminates within the interior of first injection molded coupler 308. The size and shape of first injection molded coupler 308 may be selected to facilitate its incorporation into an analyte sensor inserter (see FIG. 2), as discussed in further detail herein. It is to be appreciated that the particular size and/or shape of first injection molded coupler 308 is not especially limited.

In some embodiments, first injected molded coupler 308 may comprise leg 312 that is radially offset from longitudinal axis A. Proximal portion 306a of acupuncture needle 306 may be surrounded by leg 312, and distal portion 306b of acupuncture needle 306 may protrude into aperture 304 and beyond. Specifically, distal portion 306b may extend from leg 312 at a non-zero angle with respect to longitudinal axis A, according to certain embodiments. In addition to serving as an attachment point for acupuncture needle 306, leg 312 may serve as a 'keying feature' to facilitate proper orientation in an analyte sensor inserter. Although FIG. 3 has shown first injection molded coupler 308 as containing one leg 312, it is to be appreciated that multiple legs 312 may be present in alternative embodiments. Multiple legs 312 may provide additional keying features to facilitate assembly of an analyte sensor inserter. When multiple legs 312 are present, distal portion 306b of acupuncture needle 306 may extend from one leg 312, whereas the remainder of legs 312 do not contact acupuncture needle 306 or an additional acupuncture needle.

Figure 4B:
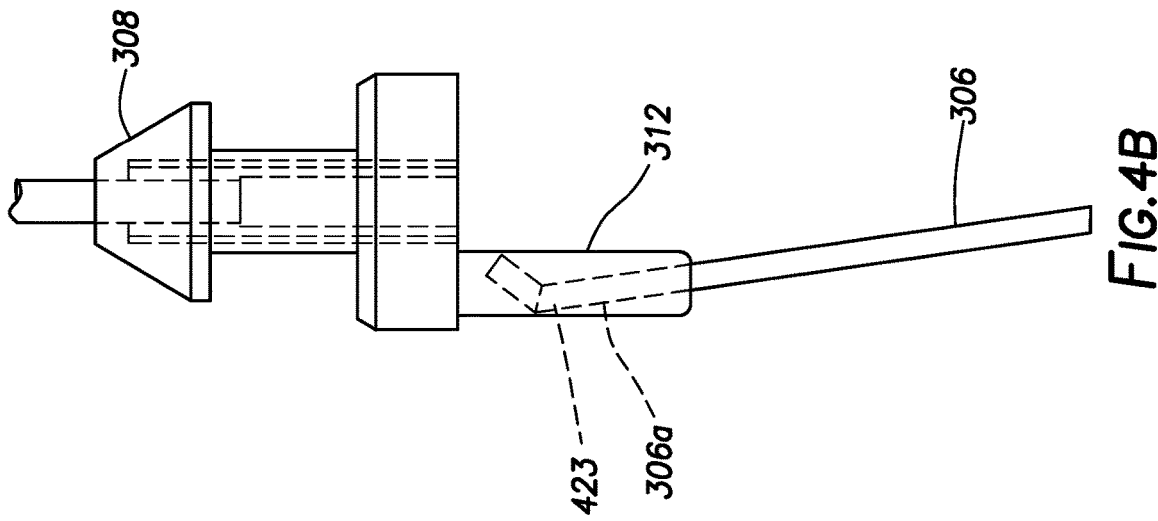
FIGS. 4A and 4B show expanded cross-sectional views of the needle assembly of FIG. 3, in which a pinch point or bend is present in the proximal portion of the acupuncture needles.
Figure 4A:
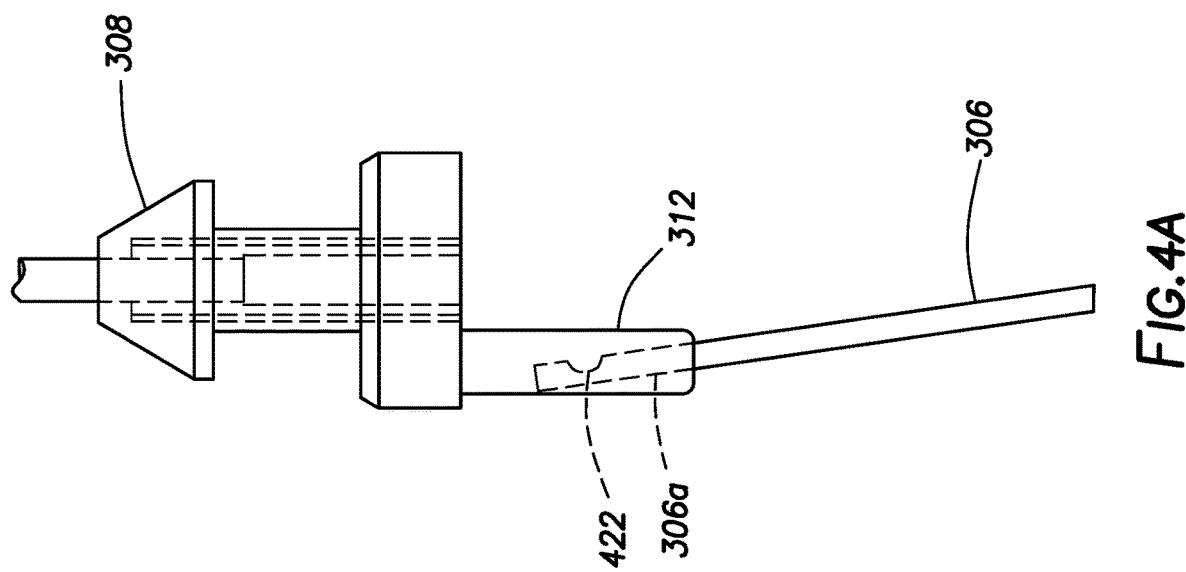

First injection molded coupler 308 and acupuncture needle 306 may be adapted to remain connected together with one another once individual acupuncture needles 306 are separated as needle constructs from needle assembly 300, as discussed in further detail below. To facilitate keeping acupuncture needle 306 connected together with first injection molded coupler 308, proximal portion 306a of acupuncture needle 306 may be modified, according to some embodiments, to promote retention within first injection molded coupler 308. Specifically, according to some embodiments, proximal portion 306a of acupuncture needle 306 may be bent, contain a pinch point, or any combination thereof to promote retention of acupuncture needle 306 within first injection molded coupler 308. The bend or pinch point creates a physical barrier to needle pullout from first injection molded coupler 308. FIGS. 4A and 4B show expanded cross-sectional views of individual acupuncture needles 306 within needle assembly 300 (FIG. 3), in which first injection molded coupler 308 includes acupuncture needle 306 with a proximal modification. Specifically, acupuncture needle 306 includes pinch point 422 within leg 312 in FIG. 4A, and in FIG. 4B, acupuncture needle 306 includes bend 423 within leg 312.

A second connection location between acupuncture needle 306 and continuous support material 302 may be present in needle assembly 300, according to some embodiments. Specifically, referring again to FIG. 3, optional second injection molded coupler 324 may surround distal portion 306b of acupuncture needle 306 and connect acupuncture needle 306 to a second location 325 upon continuous support material 302. Alternately, second injection molded coupler 324 may surround distal portion 306b without making a connection to continuous support material 302, in which case second injection molded coupler 324 may instead be considered an injection molded piece. In the two-connection configuration depicted in FIG. 3, second injection molded coupler 324 is disposed generally opposite neck 310 in aperture 304. The position of second injection molded coupler 324 may be chosen such that the insertion tip of acupuncture needle 306 is surrounded following injection molding, thereby protecting the insertion tip from damage during manipulation of acupuncture needle 306. Even when second injection molded coupler 324 is not connected to continuous support material 302, the insertion tip of acupuncture needle 306 may still be protected. The shape of second injection molded coupler 324 is not considered to be particularly limited, and the depicted generally trapezoidal configuration should not be considered as limiting the scope of the present disclosure. According to more specific embodiments, second injection molded coupler 324 may be bisected by the plane of continuous support material 302 such that a first portion of second injection molded coupler 324 is formed on a first side of the plane and a second portion of second injection molded coupler 324 is formed on a second side of the plane.

Unlike first injection molded coupler 308, second injection molded coupler 324 may be configured to establish a temporary connection between acupuncture needle 306 and continuous support material 302. More specifically, acupuncture needle 306 is configured such that it can be easily removed from second injection molded coupler 324 at a desired time, thereby freeing the insertion tip to facilitate tissue penetration, such as for insertion of an analyte sensor, for example. According to various embodiments, acupuncture needle 306 may be tapered at distal portion 306b (e.g., adjacent to the insertion tip), such that release of acupuncture needle 306 from second injection molded coupler 324 may be affected by a light pulling action. In some embodiments, either separately or in combination with tapering of distal portion 306b, a non-stick material such as a silicone or polytetrafluoroethylene coating, for example, may be applied to acupuncture needle 306 to facilitate removal from second injection molded coupler 324.

Various methods for fabricating and using the needle assemblies of the present disclosure are also contemplated herein. Methods for using the needle assemblies may include separating individual acupuncture needles arranged in a defined orientation within a needle construct and incorporating the oriented acupuncture needles into an analyte sensor inserter, as described in further detail below.

Methods for fabricating the needle assemblies of the present disclosure may comprise: providing a support material having a plurality of apertures defined therein, a neck extending from the support material into each aperture; arranging an acupuncture needle within each aperture; and injection molding polymeric material to form a first injection molded coupler that surrounds both the neck and a proximal portion of the acupuncture needle within each aperture, thereby connecting the acupuncture needle to a first location upon the support material via the neck. The needle assemblies may be fabricated such that the neck is coincident with a longitudinal axis of the first injection molded coupler, and such that the acupuncture needle is held in a pre-determined orientation with respect to the longitudinal axis, such as shown above in FIG. 3.

In more specific embodiments, the support material may comprise a continuous support material, such as a continuous metal tape.

According to some further embodiments, methods for fabricating needle assemblies of the present disclosure may further comprise injection molding polymeric material to form a second injection molded coupler that surrounds a distal portion of the acupuncture needle within each aperture and connects the acupuncture needle to a second location upon the support material. Alternately, a second injection molded coupler (injection molded piece) surrounding a distal portion of the acupuncture needle within each aperture may be fabricated similarly, but without making a connection to the support material.

Injection molding processes suitable for forming the first and second injection molded couplers will be familiar to one having ordinary skill in the art. Such processes may comprise placing one or more molds within each aperture, and injecting polymeric material into the mold(s) to form the first injection molded coupler and optionally the second injection molded coupler, wherein each injection molded coupler is positioned as described above. The first and second injection molded couplers may be formed in the same injection molding process or in separate injection molding processes. Moreover, the polymeric material used for forming the first injection molded coupler and the second injection molded coupler may be the same or different. Any suitable thermoplastic or thermosetting polymeric material may be used to form the first and second injection molded couplers. For example, in some embodiments, the first injection molded coupler may be formed from a rigid polymeric material that may facilitate use of a needle construct in an analyte sensor inserter, and the second injection molded coupler may be formed from a compliant polymeric material that may facilitate needle withdrawal at a desired time. The injection molding processes may further comprise placing an acupuncture needle within each mold prior to injecting polymeric material thereto. In some embodiments, manual or automated pick and place techniques may be used for positioning the acupuncture needle within the mold(s).

Methods for fabricating the needle assemblies of the present disclosure may further comprise, in some embodiments, die-cutting or stamping the support material to define the plurality of apertures. The apertures may be of a desired size and shape to contain the acupuncture needle and at least the first injection molded coupler. Suitable die-cutting or stamping processes will be familiar to one having ordinary skill in the art. The die-cutting or stamping process may be conducted integrally with the injection molding process(es) or in a separate production line before the injection molding process(es). In other embodiments, the support material may be obtained, sourced, or purchased with a plurality of apertures already being defined therein.

Figure 5B:
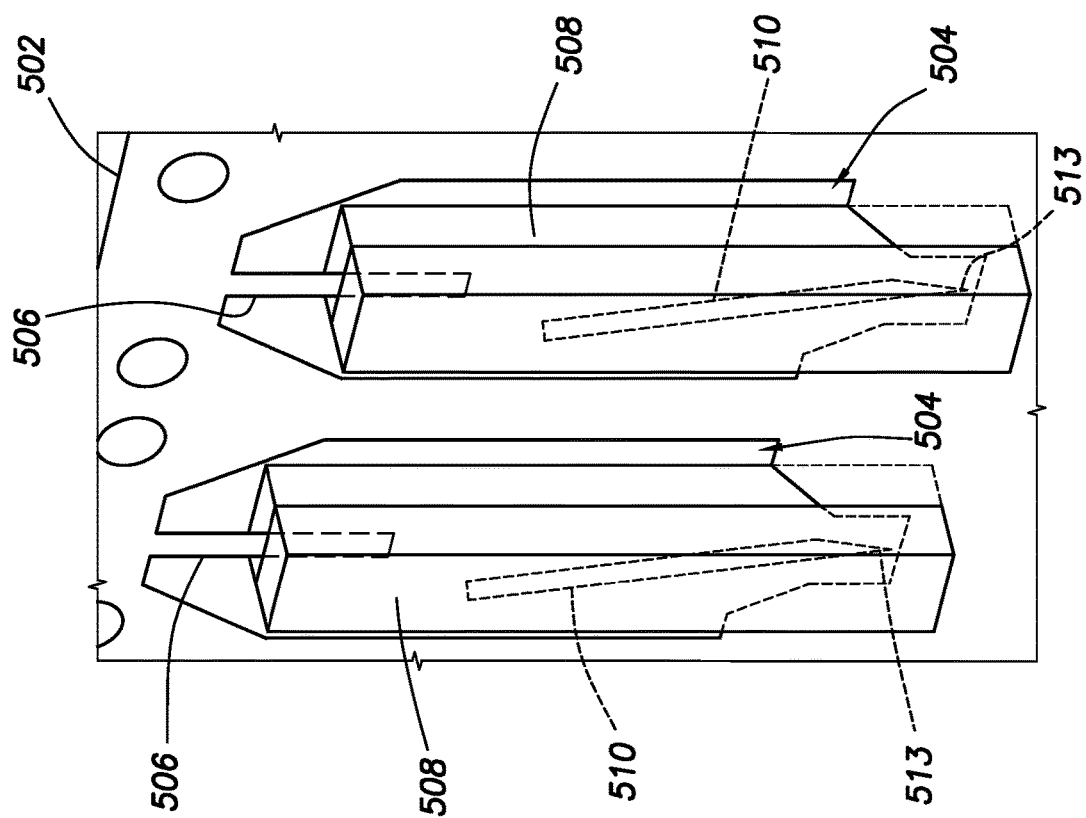
Figure 5A:
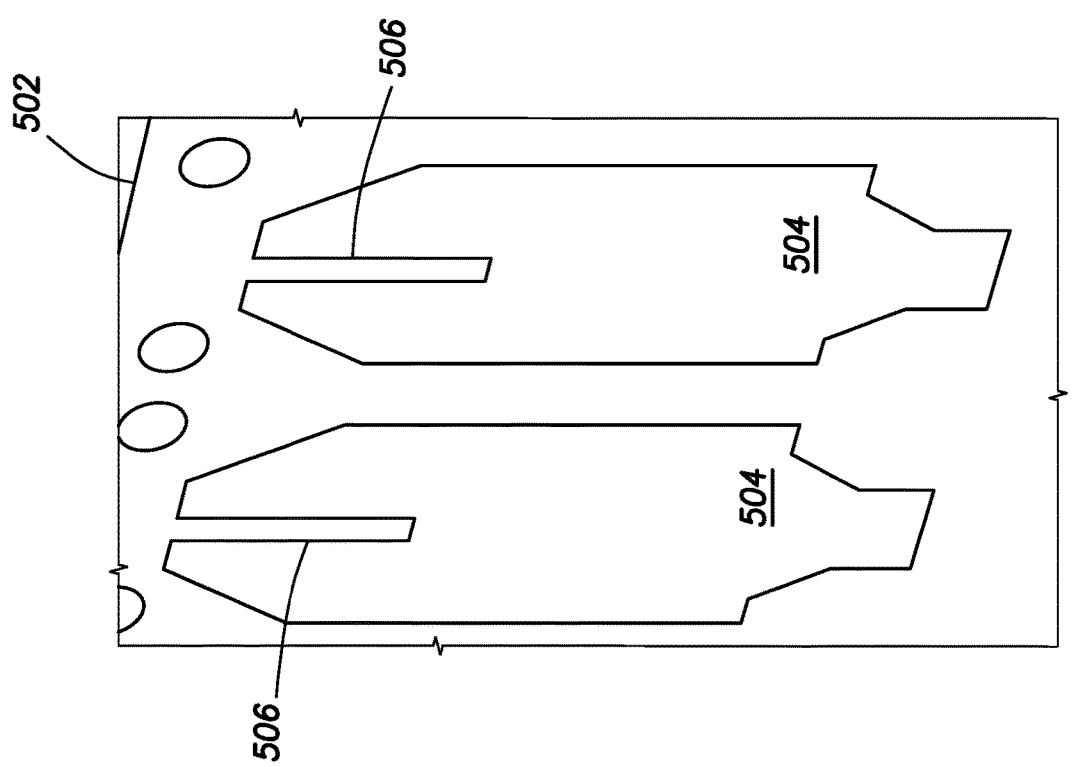

FIGS. 5A-5C show diagrams illustrating an exemplary process whereby a first configuration of needle assemblies of the present disclosure may be fabricated. In the interest of clarity, FIGS. 5A-5C show needle assembly fabrication taking place in two apertures, but it is to be appreciated that the depicted concepts may be extended to fabrication taking place in more than two apertures of a support material, either simultaneously or non-simultaneously (consecutively).

In FIG. 5A, continuous metal tape 502 having a plurality of apertures 504 of defined shape is obtained/provided (e.g., as a pre-punched tape from a commercial source) or formed (e.g., by stamping or die-cutting) prior to fabricating a needle assembly. Neck 506 extends as an elongate member into each aperture 504.

Next, as shown in FIG. 5B, mold 508, having acupuncture needle 510 positioned internally therein, is arranged within each aperture 504 in preparation for injection molding. Further details concerning mold 508 and positioning of acupuncture needle 510 therein are provided below in reference to FIGS. 7A and 7B. Neck 506 extends into mold 508 so that a connection between continuous metal tape 502 and acupuncture needle 510 occurs upon injection molding. A second connection between continuous metal tape 502 and acupuncture needle 510 may also be present distally upon acupuncture needle 510 as well.

FIG. 5C shows the next stage in the process for fabricating needle assembly 500, in which the injection molding operation(s) have been completed and mold 508 has been removed from each aperture 504. Following the injection molding operation(s), acupuncture needle 510 is connected to continuous metal tape 502 at neck 506 via first injection molded coupler 512 and optionally via second injection molded coupler 514 at the bottom of aperture 504. Second injection molded coupler 514 is removably connected to acupuncture needle 510, as described above, to aid in protecting the insertion tip during assembly fabrication and needle manipulation.

Although FIG. 5B has shown acupuncture needle 510 being contained in a single mold 510 for forming first and second injection molded couplers 512 and 514, an alternative approach may utilize second mold 511 for forming second injection molded coupler 514 around distal portion 513, without departing from the scope of the present disclosure, such as that shown in FIG. 5D.

Figure 6B:
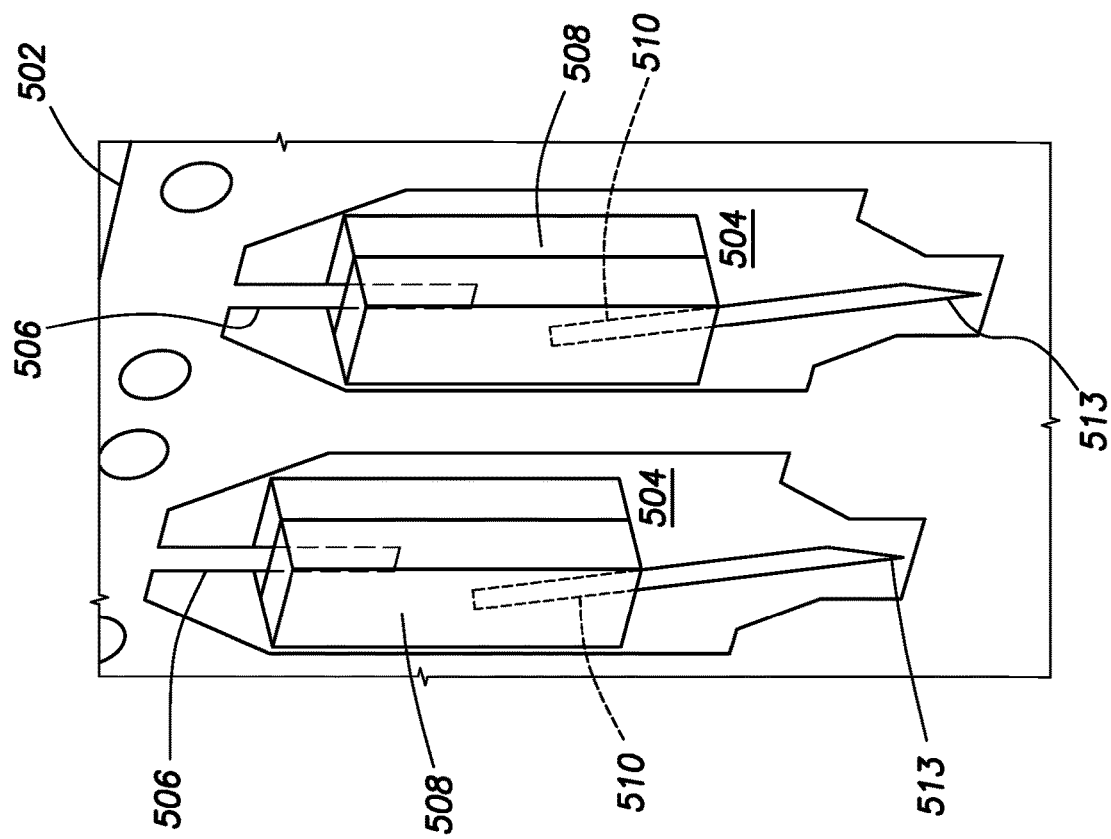
FIGS. 6A-6C show diagrams illustrating an exemplary process whereby a second configuration of needle assemblies of the present disclosure may be fabricated.
Figure 6A:
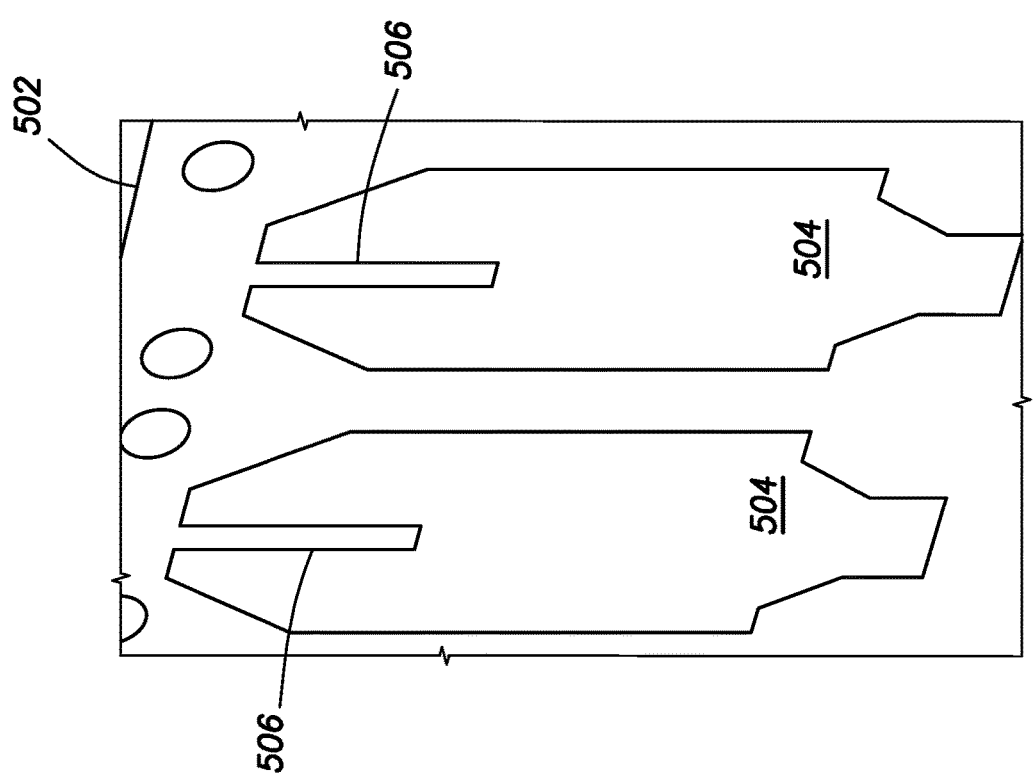
Figure 6C:
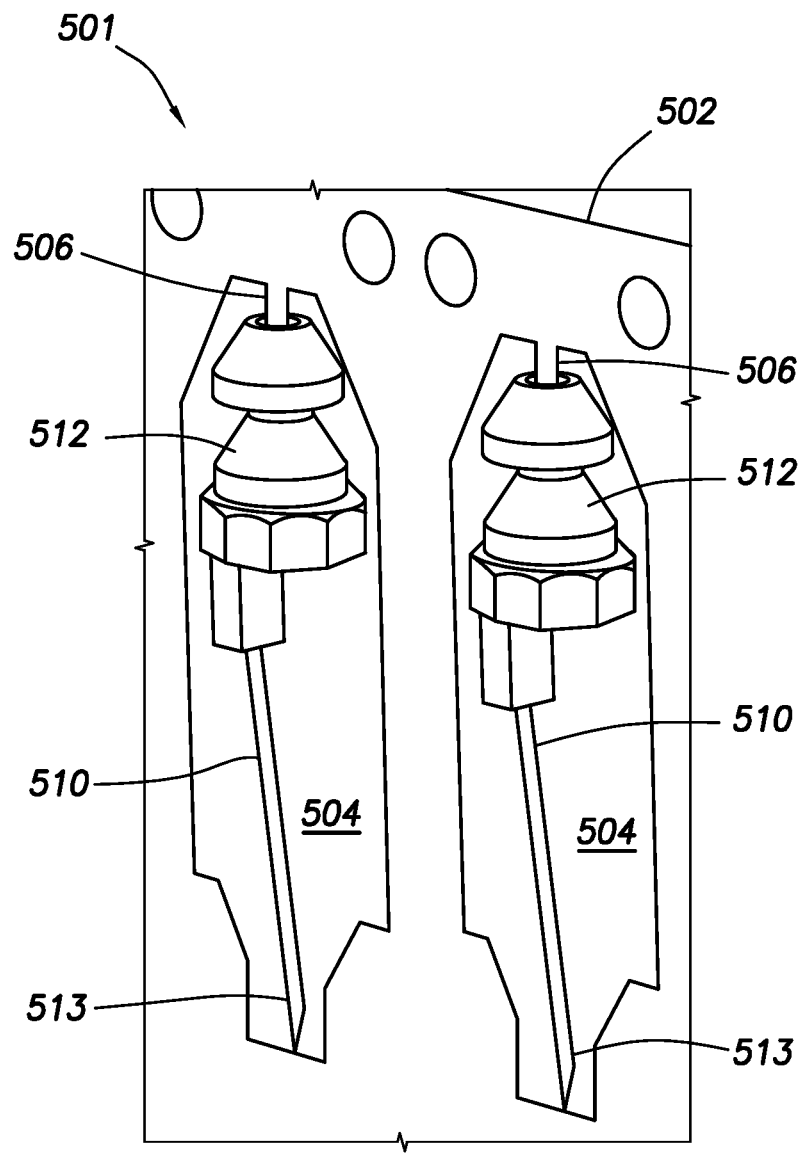

Alternately, distal portion 513 of acupuncture needle 510 may reside outside mold 508 and remain unsupported throughout the injection molding process. FIGS. 6A-6C show diagrams illustrating an exemplary process whereby a second configuration of needle assemblies of the present disclosure may be fabricated. Namely, needle assembly 501, depicted in FIG. 6C, lacks a second injection molded coupler 514, such that acupuncture needle 510 is only supported within first injection molded coupler 512 and thereby connected to continuous metal tape 502. Other than the disposition of acupuncture needle 510 within mold 508, the operations shown in FIGS. 6A-6C are similar to those shown in FIGS. 5A-5C and will accordingly not be described in detail again.

Each mold 508 has shape complementarity with each aperture 504, such that mold 508 fits therein and overlays one or more desired portions of continuous metal tape 502. When second mold 511 is used for forming second injection molded coupler 514, it may similarly overlay a bottom portion of continuous metal tape 502. According to some embodiments, mold 508 may be a two-piece mold to facilitate loading of acupuncture needle 510 therein. In such embodiments, a first piece of mold 508 is positioned adjacent to a first side of continuous metal tape 502, and a second piece of mold 508 is positioned adjacent to a second side of continuous metal tape 502. One or more cavities may be defined between the two pieces, as explained below in reference to FIGS. 7A-7C. The one or more cavities may be bisected by the plane of continuous metal tape 502. Neck 506 may extend into at least one of the cavities such that injection molding forms a connection between acupuncture needle 510 and neck 506. Although mold 508 may be a two-piece mold to facilitate loading of acupuncture needle 510, it is to be appreciated that mold 508 may be a one-piece mold in some alternative embodiments.

Figure 7B:
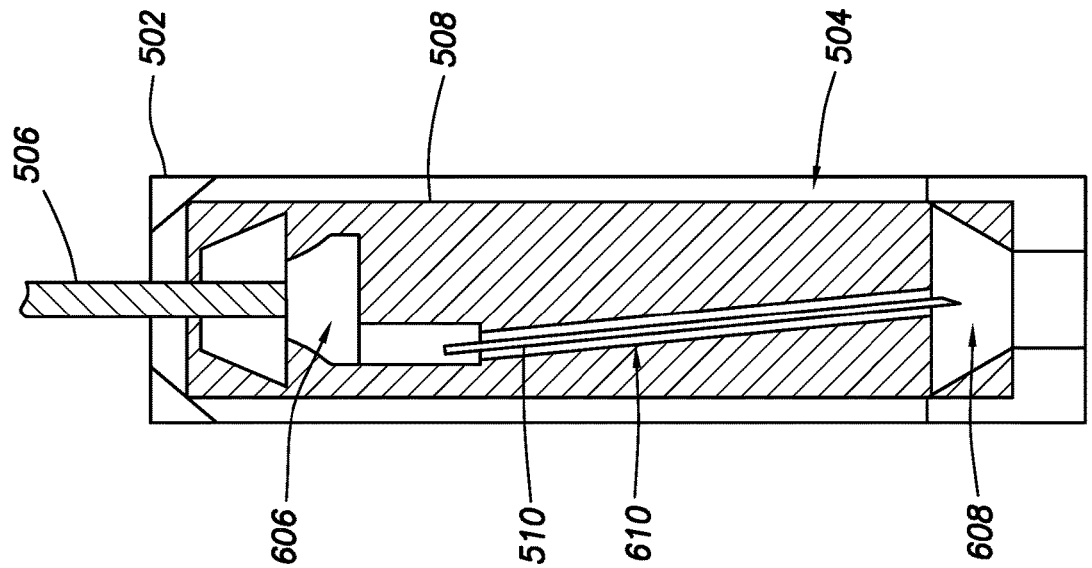
FIGS. 7A and 7B show illustrative diagrams of one hemisphere of a mold positioned within an aperture of a support material, which may be used for forming the needle assembly shown in FIG. 5C.
Figure 7A:
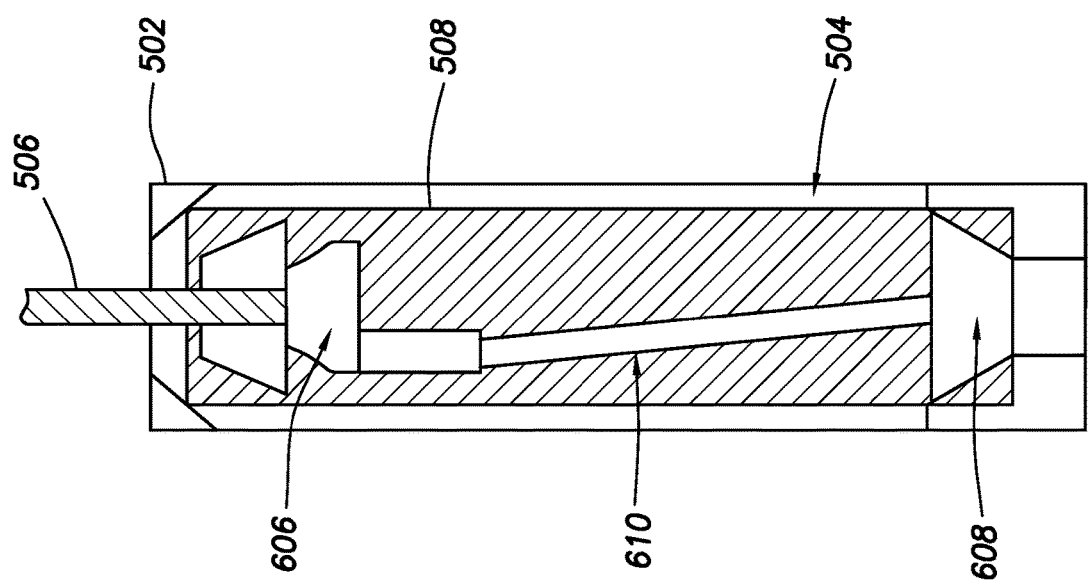

FIGS. 7A and 7B show illustrative diagrams of mold 508 arranged within aperture 504, in which a single piece (hemisphere) of mold 508 has been shown in order to display the internal details of mold 508 and the positioning of acupuncture needle 510 therein. As previously shown in FIG. 5B, the two pieces (hemispheres) of mold 508 may be assembled together in aperture 504 in preparation for injection molding.

Referring to FIG. 7A, mold 508 contains cavities 606 and 608 therein. Cavities 606 and 608 may be filled with a thermoplastic or thermosetting material during a single injection molding process or separately during two or more injection molding processes to define first injection molded coupler 512 (FIG. 5C) and second injection molded coupler 514 (FIG. 5C), respectively. Neck 506 extends into cavity 606, such that first injection molded coupler 512 (FIG. 5C) is formed in cavity 606 and surrounds neck 506. Second injection molded coupler 514 (FIG. 5C) is formed in cavity 608. Cavity 608 overlays a corresponding notch in continuous metal tape 502 at the bottom of aperture 504, such that a first portion of second injection molded coupler 514 (FIG. 5C) overlays the notch and a second portion is formed upon continuous metal tape 502. Alternately, second injection molded coupler 514 (injection molded piece) may surround distal portion 510b of acupuncture needle 510 but not form a connection to continuous metal tape 502.

Needle channel 610 extends between cavity 606 and cavity 608. Needle channel 610 is sized to receive acupuncture needle 510, as shown in FIG. 7B, such that proximal portion 510a of acupuncture needle 510 extends into cavity 606 and distal portion 510b of acupuncture needle 510 extends into cavity 608. Once injection molding has taken place to form first injection molded coupler 512 (FIG. 5C) and second injection molded coupler 514 (FIG. 5C), acupuncture needle 510 is connected to continuous metal tape 502 both distally and proximally and held in a pre-determined orientation for further manipulation. Needle channel 610 is generally not filled with thermoplastic or thermosetting material during the injection molding operation(s).

As discussed above, distal portion 510b of acupuncture needle 510 may also be unsupported, as shown for needle assembly 501 in FIG. 6C. A mold omitting needle channel

Figure 7C:
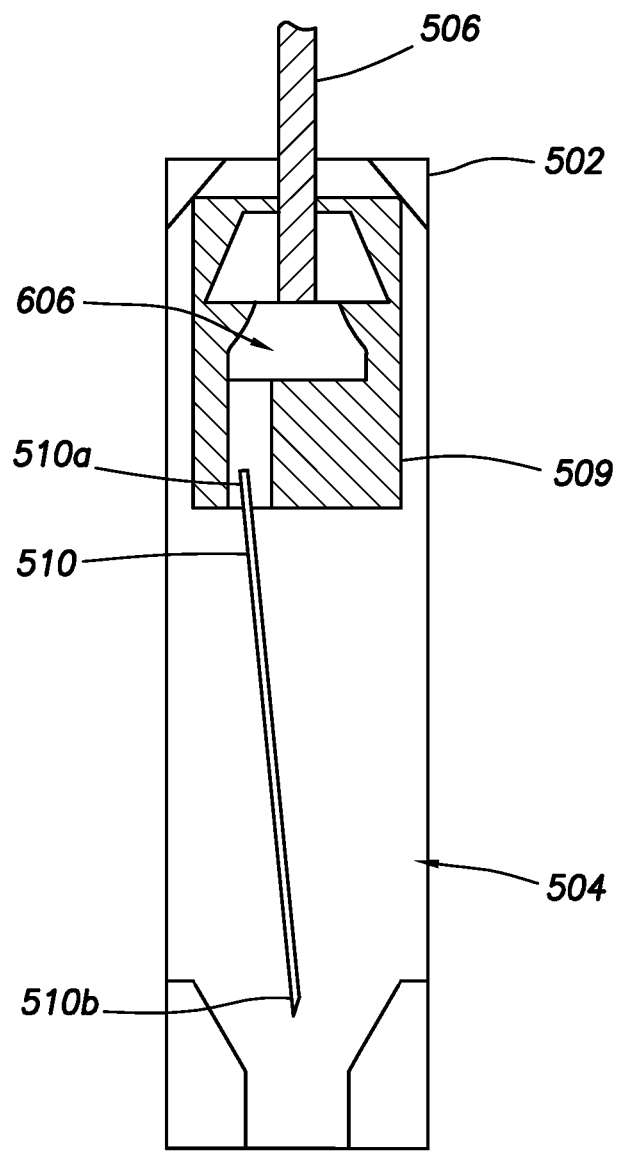
FIG. 7C shows an illustrative diagram of one hemisphere of a mold positioned within an aperture of a support material, which may be used for forming the needle assembly shown in FIG. 6C.

610 and cavity 608 may be used when forming needle assembly 501 with acupuncture needle 510 having an unsupported distal portion 510b. FIG. 7C shows an illustrative configuration for mold 509 that is suitable for forming needle assembly 501 having distal portion 510b of acupuncture needle 510 in an unsupported state.

Once injection molding is complete and each mold 508 has been removed, needle assembly 500 (FIG. 5C) or 501 (FIG. 6C) may be stored for further use or fed directly into a process for fabricating an analyte sensor inserter, such as that shown in FIG. 2. In either case, the position of each acupuncture needle 510 remains fixed with respect to first injection molded coupler 514 until further needle manipulation takes place, as described hereinbelow. In addition, the separation and orientation of each acupuncture needle 510 remains fixed with respect to one another, also facilitating further needle manipulations. In more specific embodiments, each acupuncture needle 510 may be spaced apart substantially uniformly. Since needle assembly 500 or 501 provides a highly ordered and regular arrangement of multiple acupuncture needles 510, they may be manipulated in a manner similar to that of conventional arrays of larger gauge needles or similar sharps. As such, the needle assemblies of the present disclosure may facilitate various manufacturing processes using only minor modifications of existing production lines, as described hereinafter. Namely, the needle assemblies of the present disclosure may directly replace an array of larger gauge needles or similar sharps used in present manufacturing processes.

Prior to incorporation in an analyte sensor inserter or other type of device, individual acupuncture needles 510 are removed from needle assembly 500 in the form of a needle construct. The needle construct comprises acupuncture needle 510 and first injection molded coupler 512, wherein acupuncture needle 510 remains held in a pre-determined orientation with respect to the longitudinal axis of first injection molded coupler 512, particularly non-parallel orientations with respect to the longitudinal axis. Operations to affect removal of individual needle constructs are described below in reference to FIGS. 8A and 8B. Removal of individual needle constructs may take place as a further operation of forming needle assembly 500 or as an entirely separate process, according to various embodiments.

Accordingly, in further embodiments, methods of the present disclosure may comprise separating a needle construct from the support material, such as a continuous metal tape, and the second injection molded coupler, if present, and incorporating the needle construct into an insertion device for an analyte sensor or another type of device. The needle construct comprises an acupuncture needle and the first injection molded coupler, wherein the first injection molded coupler surrounds a proximal portion of the acupuncture needle. In some embodiments, the proximal portion of the acupuncture needle may comprise a pinch point, bend, or any combination thereof to promote retention in the first injection molded coupler.

In further embodiments, separating the needle construct may comprise severing the neck adjacent to the first injection molded coupler, and pulling the distal end of the acupuncture needle from the second injection molded coupler. In embodiments wherein the second injection molded coupler is not present, severing the neck adjacent to the first injection molded coupler directly releases the needle construct from the needle assembly. Severing the neck to release the needle construct leaves a metal core within the first injection molded coupler, wherein the metal core may be coincident with the longitudinal axis of the first injection molded coupler. Once separated from the needle assembly, the individual needle constructs may be further manipulated into a production line.

As shown in FIG. 8A, neck 506 may be severed to break the first connection to continuous metal tape 502. Severing of neck 506 may take place using any suitable method, such as guillotine cutting, die cutting, scissor cutting, or the like. Once neck 506 has been severed, first injection molded coupler 514 and acupuncture needle 510 are free to move together along longitudinal axis A. Application of a gentle axial pulling force F (shown with block arrow) along longitudinal axis A may be sufficient to dislodge acupuncture needle 510 from second injection molded coupler 514, thereby freeing needle construct 700 (FIG. 8B). Similar operations may be used to separate needle construct 700 in embodiments either lacking second injection molded coupler 514 or having second injection molded coupler 514 that is unconnected to metal tape 502, such as in needle assembly 501. Needle construct 700 includes acupuncture needle 510 held in a defined configuration with respect to first injection molded coupler 512, as discussed herein.

Embodiments disclosed herein include:

A. Needle assemblies. The needle assemblies comprise: a support material having a plurality of apertures defined therein; and a first injection molded coupler located within each aperture that surrounds a proximal portion of an acupuncture needle and connects the acupuncture needle to a first location upon the support material; wherein the acupuncture needle is held in a pre-determined orientation with respect to a longitudinal axis of the first injection molded coupler.

B. Needle constructs. The needle constructs comprise: an acupuncture needle having a proximal portion surrounded by an injection molded piece; wherein the acupuncture needle is oriented non-parallel with respect to a longitudinal axis of the injection molded piece.

C. Methods for forming and manipulating a needle assembly. The methods comprise: providing a support material having a plurality of apertures defined therein, a neck extending from the support material into each aperture; arranging an acupuncture needle within each aperture; and injection molding polymeric material to form a first injection molded coupler that surrounds both the neck and a proximal portion of the acupuncture needle within each aperture, thereby connecting the acupuncture needle to a first location upon the support material; wherein the neck is coincident with a longitudinal axis of the first injection molded coupler; and wherein the acupuncture needle is held in a pre-determined orientation with respect to the longitudinal axis.

Each of embodiments A, B, and C may have one or more of the following additional elements in any combination.

Element 1: wherein the support material comprises a continuous metal tape.

Element 2: wherein a neck extends from the support material into each aperture; wherein the first injection molded coupler surrounds the neck, such that the neck is coincident with the longitudinal axis.

Element 3: wherein the needle assembly further comprises: a second injection molded coupler located within each aperture that surrounds a distal portion of the acupuncture needle and connects the acupuncture needle to a second location upon the support material.

Element 4: wherein the acupuncture needle is held non-parallel with respect to the longitudinal axis.

Element 5: wherein the acupuncture needle is held at an angle ranging between about 5° and about 15° with respect to the longitudinal axis.

Element 6: wherein the proximal portion of the acupuncture needle is bent, contains a pinch point, or any combination thereof.

Element 7: wherein the first injection molded coupler comprises a leg that is radially offset from the longitudinal axis; wherein the proximal portion of the acupuncture needle is surrounded by the leg and a distal portion of the acupuncture needle extends from the leg at a non-zero angle with respect to the longitudinal axis.

Element 8: wherein the support material comprises a continuous metal tape, a neck extends from the continuous metal tape into each aperture, and the first injection molded coupler surrounds the neck, such that the neck is coincident with the longitudinal axis.

Element 9: wherein the acupuncture needle ranges between about 0.1 mm and about 0.6 mm in diameter.

Element 10: wherein acupuncture needles in adjacent apertures are spaced apart substantially uniformly.

Element 11: wherein the needle construct further comprises: a metal core within the injection molded piece that is coincident with the longitudinal axis.

Element 12: wherein the method further comprises: injection molding polymeric material to form a second injection molded coupler that surrounds a distal portion of the acupuncture needle and connects the acupuncture needle to a second location upon the support material.

Element 13: wherein the method further comprises: separating a needle construct from the support material and the second injection molded coupler, the needle construct comprising the acupuncture needle and the first injection molded coupler; and incorporating the needle construct into an insertion device for an analyte sensor.

Element 14: wherein separating the needle construct comprises severing the neck adjacent to the first injection molded coupler, and pulling the distal end of the acupuncture needle from the second injection molded coupler.

Element 15: wherein the method further comprises: separating a needle construct from the support material, the needle construct comprising the acupuncture needle and the first injection molded coupler; and incorporating the needle construct into an insertion device for an analyte sensor.

Element 16: wherein separating the needle construct comprises severing the neck adjacent to the first injection molded coupler.

Element 17: wherein the needle assembly further comprises: an injection molded piece located within each aperture that surrounds a distal portion of the acupuncture needle.

Element 18: wherein the method further comprises: separating a needle construct from the support material, the needle construct comprising the acupuncture needle and the first injection molded coupler; and incorporating the needle construct into an insertion device for an analyte sensor.

By way of non-limiting example, exemplary combinations applicable to A, B, and C include: The needle assembly of A in combination with elements 1 and 2; 1 and 3; 1 and 4; 1 and 5; 1 and 6; 1 and 7; 1 and 9; 1 and 10; 1 and 17; 2 and 3; 2 and 4; 2-4; 2 and 5; 2, 3 and 5; 2 and 6; 2 and 7; 2 and 9; 2 and 10; 2 and 17; 3 and 4; 3 and 5; 3 and 6; 3 and 7; 3 and 8; 3 and 9; 3 and 10; 3 and 17; 4 and 6; 4 and 7; 4 and 8; 4 and 9; 4 and 10; 4 and 17; 5 and 6; 5 and 7; 5 and 8; 5 and 9; 5 and 10; 5 and 17; 6 and 7; 6 and 8; 6 and 9; 6 and 10; 6 and 17; 7 and 8; 7 and 9; 7 and 10; 7 and 17; 8 and 9; 8 and 10; 8 and 17; 9 and 17 and 9 and 10. The needle construct of B in combination with elements 5 and 6; 5 and 7; 5 and 9; 5 and 11; 6 and 7; 6 and 9; 6 and 11; 7 and 9; 7 and 11; and 9 and 11. The method of C in combination with elements 1 and 4; 1 and 5; 1 and 6; 1 and 7; 1 and 9; 1 and 10; 1 and 12; 1, 12 and 13; 1 and 12-14; 1 and 15; 1 and 18; 1, 15 and 16; 4 and 6; 4 and 7; 4 and 9; 4 and 10; 4 and 12; 4, 12 and 13; 4 and 12-14; 4 and 15; 4 and 18; 4, 15 and 16; 5 and 6; 5 and 7; 5 and 9; 5 and 10; 5 and 12; 5, 12 and 13; 5 and 12-14; 5 and 15; 5 and 18; 5, 15 and 16; 6 and 7; 6 and 9; 6 and 10; 6 and 12; 6, 12 and 13; 6 and 15; 6 and 18; 6, 15 and 16; 7 and 9; 7 and 10; 7 and 12; 7, 12 and 13; 7 and 15; 7 and 18; 7, 15 and 16; 9 and 10; 9 and 12; 9, 12 and 13; 9 and 15; 9 and 18; 9, 15 and 16; 10 and 12; 10, 12 and 13; 10 and 15; 10 and 18; 10, 15 and 16; 12 and 13; 12-14; and 15 and 16.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A needle assembly comprising:
    a support material having a plurality of apertures defined therein and a plurality of necks, wherein a neck of the plurality of necks extends from the support material into each aperture; and
    a first injection molded coupler located within each aperture that surrounds a portion of a first neck of the plurality of necks and a proximal portion of an acupuncture needle, wherein the first injection molded coupler connects the acupuncture needle to a first location upon the support material;
    wherein the acupuncture needle is held in a pre-determined orientation with respect to a longitudinal axis of the first injection molded coupler,
    wherein a portion of the acupuncture needle extending from the first injection molded coupler is held non-parallel with respect to the longitudinal axis of the first injection molded coupler.
2. The needle assembly of claim 1, wherein the support material comprises a continuous metal tape.
3. The needle assembly of claim 1,
    wherein the first neck is coincident with the longitudinal axis in the first injection molded coupler.
4. The needle assembly of claim 1, wherein the acupuncture needle is held non-parallel with respect to the longitudinal axis.
5. The needle assembly of claim 4, wherein the acupuncture needle is held at an angle ranging between about 5° and about 15° with respect to the longitudinal axis.
6. The needle assembly of claim 1, further comprising:
    a second injection molded coupler located within each aperture that surrounds a distal portion of the acupuncture needle and connects the acupuncture needle to a second location upon the support material.
7. The needle assembly of claim 1, wherein the proximal portion of the acupuncture needle is bent, contains a pinch point, or any combination thereof.
8. The needle assembly of claim 1, wherein the first injection molded coupler comprises a leg that is radially offset from the longitudinal axis;
    wherein the proximal portion of the acupuncture needle is surrounded by the leg and a distal portion of the acupuncture needle extends from the leg at a non-zero angle with respect to the longitudinal axis.
9. The needle assembly of claim 1, wherein the support material comprises a continuous metal tape, each neck extends from the continuous metal tape into each aperture, and the first injection molded coupler surrounds the first neck, such that the first neck is coincident with the longitudinal axis.
10. The needle assembly of claim 1, wherein the acupuncture needle ranges between about 0.1 mm and about 0.6 mm in diameter.
11. The needle assembly of claim 1, wherein acupuncture needles in adjacent apertures are spaced apart substantially uniformly.
12. The needle assembly of claim 1, further comprising:
    an injection molded piece located within each aperture that surrounds a distal portion of the acupuncture needle.
13. A method comprising:
    providing a support material having a plurality of apertures defined therein, a neck extending from the support material into each aperture;
    arranging an acupuncture needle within each aperture; and
    injection molding polymeric material to form a first injection molded coupler that surrounds both the neck and a proximal portion of the acupuncture needle within each aperture, thereby connecting the acupuncture needle to a first location upon the support material;
    wherein the neck is coincident with a longitudinal axis of the first injection molded coupler; and
    wherein the acupuncture needle is held in a pre-determined orientation with respect to the longitudinal axis.
14. The method of claim 13, wherein the support material comprises a continuous metal tape.
15. The method of claim 13, wherein the acupuncture needle is held non-parallel with respect to the longitudinal axis.
16. The method of claim 13, further comprising:
    injection molding polymeric material to form a second injection molded coupler that surrounds a distal portion of the acupuncture needle and connects the acupuncture needle to a second location upon the support material.
17. The method of claim 13, further comprising:
    separating a needle construct from the support material, the needle construct comprising the acupuncture needle and the first injection molded coupler; and
    incorporating the needle construct into an insertion device for an analyte sensor.

* * * * *